United States Patent
Hagness et al.

(10) Patent No.: US 12,303,687 B2
(45) Date of Patent: *May 20, 2025

(54) IN VIVO GENE THERAPY DELIVERY PROCEDURE AND DEVICE

(71) Applicant: Wisconsin Alumni Research Foundation, Madison, WI (US)

(72) Inventors: Susan Hagness, Madison, WI (US); Erik Aiken, Madison, WI (US); John Booske, McFarland, WI (US); Hans Sollinger, Madison, WI (US); Paul Laeseke, Madison, WI (US); Tausif Alam, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/987,578

(22) Filed: Nov. 15, 2022

(65) Prior Publication Data

US 2023/0074581 A1 Mar. 9, 2023

Related U.S. Application Data

(63) Continuation of application No. 17/160,832, filed on Jan. 28, 2021, now Pat. No. 11,839,761, which is a
(Continued)

(51) Int. Cl.
*A61M 25/10* (2013.01)
*A61K 48/00* (2006.01)
(Continued)

(52) U.S. Cl.
CPC .......... *A61N 1/327* (2013.01); *A61K 48/0083* (2013.01); *A61M 25/10* (2013.01);
(Continued)

(58) Field of Classification Search
CPC ........ A61N 1/327; A61N 1/325; A61N 1/306; A61B 2018/0022; A61B 2018/0025; A61B 2018/00261; A61M 2025/1052
See application file for complete search history.

(56) References Cited

U.S. PATENT DOCUMENTS

| | | | |
|---|---|---|---|
| 6,593,130 B1 * | 7/2003 | Sen ........................ | A61N 1/325 604/21 |
| 8,500,713 B2 * | 8/2013 | Ferek-Petric .......... | A61N 1/325 604/890.1 |

(Continued)

*Primary Examiner* — Laura A Bouchelle
(74) *Attorney, Agent, or Firm* — Boyle Frederickson, SC

(57) ABSTRACT

A "localizable" systemic gene therapy system is provided substantially increasing the transfection efficiency of the gene vectors into targeted tissue cells and substantially reducing the escape of the gene vectors from the targeted tissue volume, such as would waste the vectors, promote undesired immune reactions, and/or incur prohibitive costs for the required dose of gene-containing virus vectors. In this regard, the invention provides a means to simultaneously achieve local electroporation and gene-containing vector injection in a portion of a vascularized organ. It includes two double-balloon catheters that create contained volumes in parallel blood vessels for the introduction of vectors with reduced loss along with electrodes providing electroporation of the cells in the same location where the vectors are injected.

19 Claims, 3 Drawing Sheets

Related U.S. Application Data continuation of application No. 16/043,461, filed on Jul. 24, 2018, now Pat. No. 10,918,861.

(51) Int. Cl.
*A61N 1/32* (2006.01)
*A61M 3/00* (2006.01)
*A61M 31/00* (2006.01)
*A61N 1/30* (2006.01)
*C12N 15/63* (2006.01)

(52) U.S. Cl.
CPC .............. *A61N 1/325* (2013.01); *A61M 3/00* (2013.01); *A61M 2025/1052* (2013.01); *A61M 31/00* (2013.01); *A61N 1/306* (2013.01); *C12N 15/63* (2013.01)

(56) References Cited

U.S. PATENT DOCUMENTS

| | | | |
|---|---|---|---|
| 10,918,861 B2 * | 2/2021 | Hagness | A61M 25/10 |
| 11,839,761 B2 * | 12/2023 | Hagness | A61K 48/0083 |
| 2016/0296674 A1 * | 10/2016 | Rubanyi | A61B 17/12136 |

* cited by examiner

IN VIVO GENE THERAPY DELIVERY PROCEDURE AND DEVICE

CROSS REFERENCE TO RELATED APPLICATION

This application is a continuation of U.S. patent application Ser. No. 17/160,832 filed Jan. 28, 2021, which is a continuation of U.S. patent application Ser. No. 16/043,461 filed Jul. 24, 2018, each of which is hereby incorporated by reference.

BACKGROUND OF THE INVENTION

The present invention relates to a method and apparatus for gene therapy, and more particularly, an improved gene therapy delivery system.

Genetic mutation based metabolic diseases significantly reduce quality of life for hundreds of millions of people in the world and account for 70% of child hospitalizations and 10% of adult hospitalizations. There are hundreds of such diseases, including diabetes, cystic fibrosis, sickle cell anemia, hemophilia, and thalassemia. Many of them involve the liver due to its central role in metabolism.

Gene therapy has been found to be a promising cure for these diseases by transducing functional genes (i.e, a functional portion of a DNA sequence) into a small portion of cells within the target organ, for example, liver cells, thus correcting the inherited metabolic discrepancy. It has been found that only a small fraction of liver cells (hepatocytes) need to be converted, for example, about 5% in the liver, in order to produce therapeutic gene products sufficient to cure the disease.

A carrier of gene, such as a viral vector, can be used to deliver foreign, functional genes into cells. By transferring the functional gene into a virus that either enters the cell membrane through endocytosis (viruses without a viral envelope) or binds to receptors on the cell membrane and fuses with the cell membrane thus releasing the genetic material (viruses with a viral envelope), genes can be introduced into the cell. Depending on the virus used to deliver the gene, the viral genetic material either integrates into a chromosome of the cell or persists episomally without integration within the nucleus of the cell and expresses the introduced gene to treat the genetic defect.

Systemic gene therapy, which delivers functional genes via the circulatory system, has been found to be a successful delivery method for functional genes in small mammals (smaller than an average dog). However, this treatment has not been found to be scalable to large mammals for three reasons:

First, inefficient transduction of target cells necessitates large, cost-prohibitive gene vector doses. The larger size of the animal and more extensive blood flow pathways necessitates much larger doses of expensive vectors in order to convert the necessary amount of hepatocytes for effective therapy.

Second, the patient may have pre-existing antibodies that neutralize a virus capsid used as a gene vector rendering therapeutic attempt less effective or ineffective.

Third, systemic injection of such large quantities of the virus vector can trigger adaptive immunity that destroys not only the virus but also the genetically modified cells.

Compensating for these problems by introducing large amounts of vector is impractical because of the high expense of producing the vector and the inherent risks associated with injecting large amounts of virus into a patient.

SUMMARY OF THE INVENTION

The present invention provides a "localizable" liver gene therapy system substantially reducing the escape of the gene vectors from the liver, such that the waste of vector through systemic dilution is minimized, which would limit the undesired immune reactions. In this regard, the invention describes a two inflatable balloon catheter that creates a finite contained volume along coextending blood vessels to increase the local concentration of virus for increased uptake of vectors in the nearby tissue with reduced vector loss. While the contained volumes would seem to be counter to the intent of treating a large amount of tissue, electrodes in adjacent blood vessels are used to produce electroporation in the tissue region between the electrodes offsetting this localization of delivery and improving uptake of the vector.

Generally, a pair of catheters is inserted into a venous access site for hepatic vein catheterization. The medical professional may visualize the hepatic vein using ultrasound or x-ray (fluoroscopy) guidance to advance the catheter into coextending blood vessels of the liver. A pair of inflated balloons flanking an active delivery section of the catheter may secure the location and positioning of the catheter's active delivery section while also containing the vector volumes. Viral vectors are then injected through the pair of catheters to pass outward through holes in the active delivery section of the catheters to define a gene delivery area. An electrical charge is delivered to create a voltage between electrodes of the pair of catheters and an electric field commensurate with the gene delivery area. This results in an improved transduction rate of the viral vectors into the hepatic cells and therefore improved conversion of the hepatocytes with smaller vector doses.

The present invention provides gene therapy delivery system including a first balloon catheter providing a distal end having a first and second inflatable balloon spaced apart along the distal end to define an intervening catheter section and at least one passageway through a delivery lumen of the intervening catheter section for the delivery of a gene vector; a second balloon catheter providing a distal end having a first and second inflatable balloon spaced apart along the distal end to define an intervening catheter section and at least one passageway through a delivery lumen of the intervening catheter section for the delivery of a gene vector; a first electrode extending along the first balloon catheter; a second electrode extending along the second balloon catheter; and a power supply providing a voltage across the first and second balloon catheters.

It is thus a feature of at least one embodiment of the invention to reduce the cost-prohibitive gene vector doses for targeted high efficiency delivery by eliciting electroporation across a large area of tissue not just within the blood vessel.

The first and second electrode may extend within the delivery lumen of the first and second balloon catheter, respectively.

It is thus a feature of at least one embodiment of the invention to prevent electrical charge from passing through tissue or to expose blood or tissue to conductive wires.

The first and second electrode may terminate before a distal tip of the first and second balloon catheters, respectively.

It is thus a feature of at least one embodiment of the invention to isolate the electric field to the intervening catheter section between the two balloons.

The first and second electrode may extend substantially parallel with a catheter sidewall.

It is thus a feature of at least one embodiment of the invention to use wire electrodes that still provide clearance within the catheter lumen for vector flow.

The first and second electrode may provide a coaxial conductor having an inner and outer coaxial conductive element and wherein the outer conductive element is removed from the coaxial conductor within the intervening catheter section to allow transmission of electrical field for electroporation. A proximal end of the catheter may provide an electrical connector providing separate connections to the inner and outer coaxial conductive elements. The inner conductive element may be any biocompatible conductive metal, such as, but not limited to, stainless steel.

It is thus a feature of at least one embodiment of the invention to isolate the electric field between the intervening catheter sections of the first and second catheters.

The first and second electrode may provide a coaxial conductor wherein the coaxial conductor is insulated within the intervening catheter section to prevent current flow to an exterior of the first and second balloon catheters.

It is thus a feature of at least one embodiment of the invention to protect the surrounding tissue from damage.

The intervening catheter section includes a plurality of perfusion holes spaced along the intervening catheter section. The intervening catheter section may include at least one perfusion hole centered within the intervening catheter section.

It is thus a feature of at least one embodiment of the invention to optimize delivery of the viral vector to a large tissue area surrounding the blood vessel.

The catheter may have at least two lumens, one communicating with at least one of the balloon catheters and the other communicating with the delivery lumen. One of the first and second inflatable balloon may be positioned at a distal tip of the first and second balloon catheters.

It is thus a feature of at least one embodiment of the invention to independently inflate the balloons separate from the flow of vector through the catheter for independent control.

The present invention also provides a method of gene therapy having the following steps: providing a first balloon catheter providing a distal end having a first and second inflatable balloon spaced apart along the distal end to define an intervening catheter section and at least one passageway through a delivery lumen of the intervening catheter section for the delivery of a gene vector, a first electrode extending along the first balloon catheter; providing a second balloon catheter providing a distal end having a first and second inflatable balloon spaced apart along the distal end to define an intervening catheter section and at least one passageway through a delivery lumen of the intervening catheter section for the delivery of a gene vector, a second electrode extending along the second balloon catheter; inserting the first balloon catheter into a first blood vessel of a patient; inserting the second balloon catheter into a second blood vessel of the patient; injecting a gene vector through the delivery lumen of the intervening catheter section to deliver the gene vector into surrounding cells; and delivering an electrical charge to one of the first and second electrodes to produce a voltage across between the first and second balloon catheter.

One of the first and second electrodes may be a return electrode. The first and second electrical conductor electrodes may be separated by an average distance of 5-30 mm.

It is thus a feature of at least one embodiment of the invention to electroporate a larger area of liver cells, coextensive with the tissue area between electrodes for improved uptake of vector.

These particular objects and advantages may apply to only some embodiments falling within the claims and thus do not define the scope of the invention.

DETAILED DESCRIPTION OF THE PREFERRED EMBODIMENT

Figure 1:
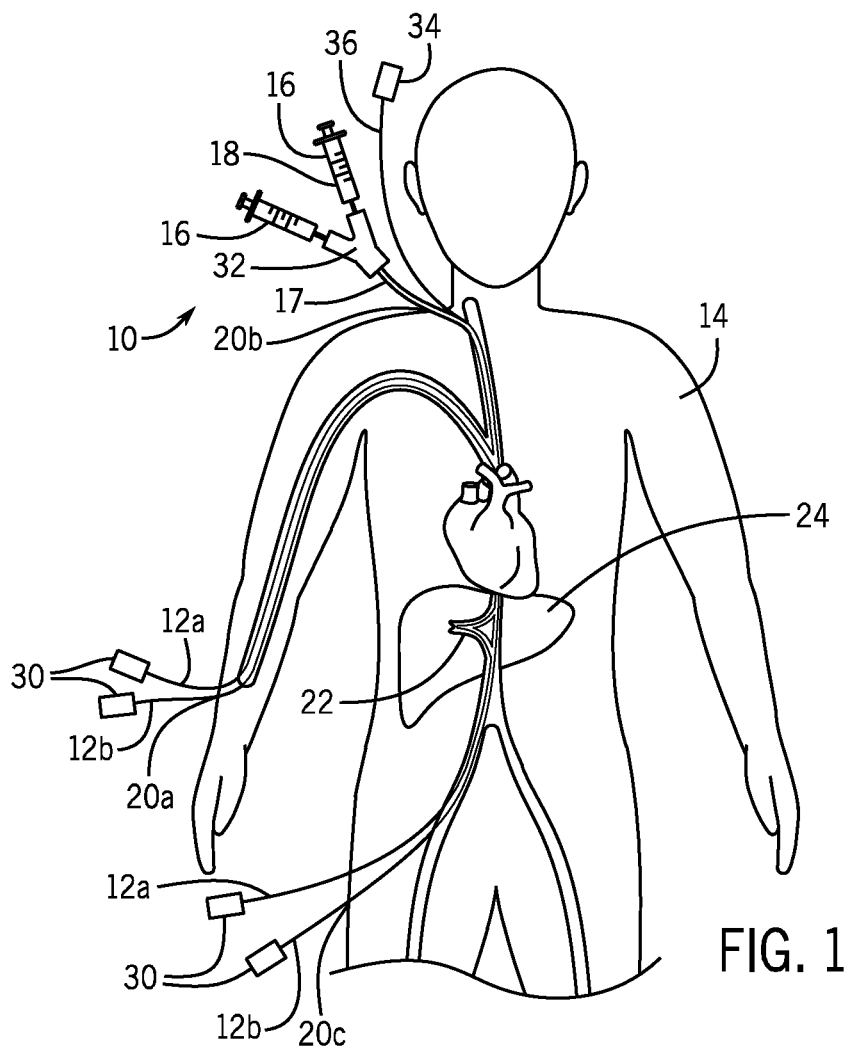
FIG. 1 is a front view of a human receiving intravenous gene delivery through catheterization of a hepatic vein of the liver through venous access sites of the body.

Referring now to FIG. 1, a gene therapy delivery system 10 may include at least two catheters 12, and preferably a pair of catheters 12a, 12b, inserted within the body to deliver fluids containing genes to a target organ of a human patient 14 for transduction into cells. The fluids may be intravenously injected by a syringe 16 or a pump (not shown) into a proximal end 17 of the catheter 12 extending outside of the body and into a catheter insertion site. The fluids may include viral vectors 18, for example, retroviruses, lentiviruses, adenoviruses, adeno-associated viruses, and the like containing functional genes for gene therapy.

While the present invention is illustrated as a gene therapy delivery system 10, it is understood that the delivery system 10 may also be used to deliver drugs, for example, to a tissue or tumor site.

The catheter 12 may be inserted into a peripheral or central vein of the human patient 14 through a venous access site 20 allowing for catheterization of a hepatic vein 22 of the liver 24 of the human patient 14, for example, at the antecubital vein 20a, the jugular vein 20b, or the femoral vein 20c. As illustrated, the catheter 12 may be inserted at an incision inside the neck of the human patient 14 proximate to the jugular vein 20b and then drawn downward through the hepatic vein 22 into the liver 24. The medical professional may use a guide wire (not shown) to facilitate placement of the catheter 12 allowing the catheter 12 to be installed over the guide wire after placement of the guide wire. This catheterization process may also be facilitated by real-time visualization by a medical professional through ultrasound or x-ray (fluoroscopy) guidance.

Figure 3:
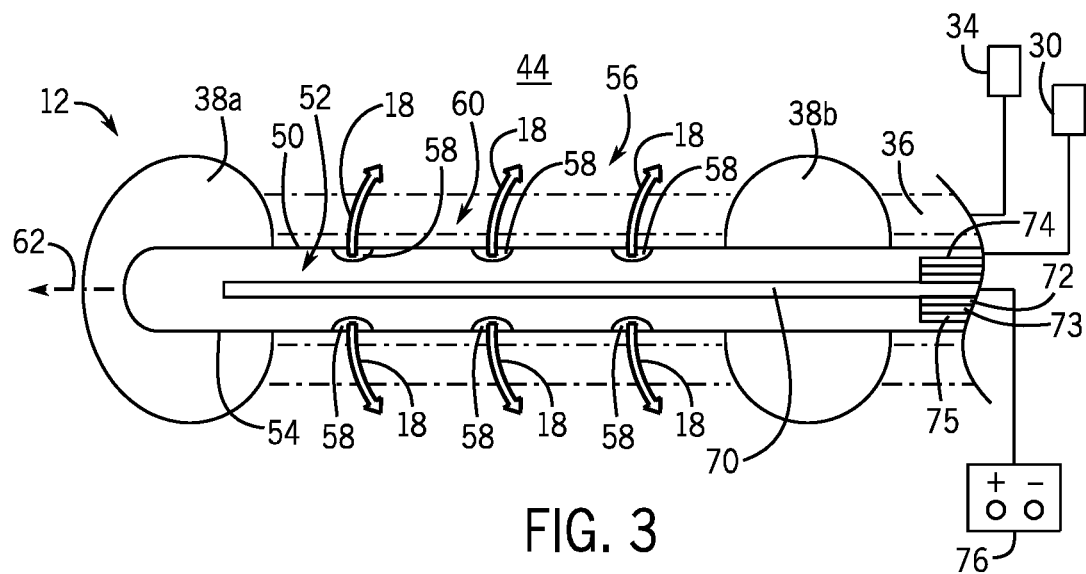
FIG. 3 is a cross sectional view of one of the catheters of the present invention having an active delivery portion flanked by occlusion balloons and a conductor electrode extending through the lumen of the catheter to effectuate an electric field with a second catheter.

Referring also to FIG. 3, each catheter 12 may include at least one proximal port 30, for example, two proximal ports 30 connected by a Y connector 32, allowing different fluids to be injected into the catheter 12. The catheter 12 may also provide a separate balloon inflation port 34 and balloon inflation tube 36 co-extending with and substantially parallel to the catheter 12 to provide inflation of one or more balloons 38 of the catheter 12, as further described below. The balloon inflation port 34 may also include a valve controlling flow through the tube 36 to inflate or deflate the balloons 38 as desired.

While it is shown that the catheter 12 is installed into the hepatic vein 22 of the liver 24 of the human patient 14 for gene therapy, it is understood that the catheter 12 may also catheterize other organs or tissues of the human patient 14 such as the kidney or pancreas.

Figure 2:
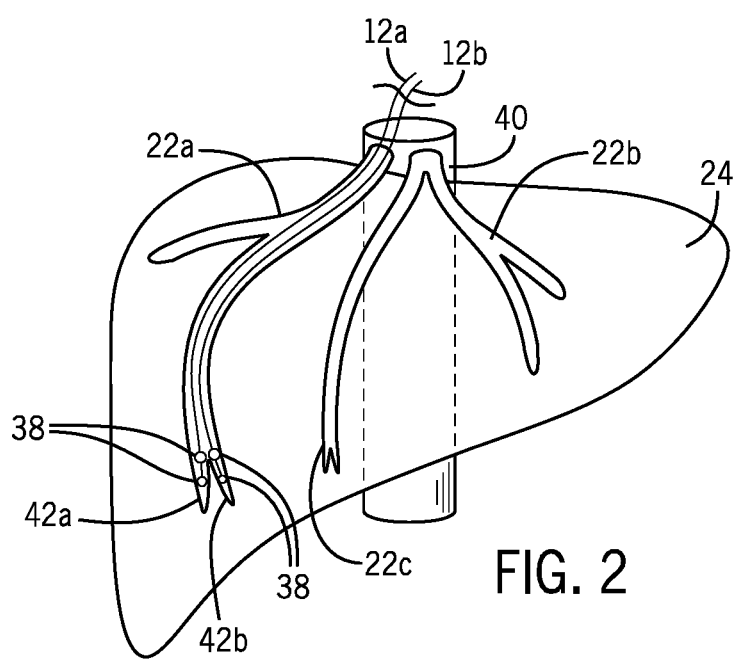
FIG. 2 is a perspective view through the liver of the human of FIG. 1 after insertion of a pair of catheters in two separate hepatic veins of the liver.

Referring now to FIG. 2, each catheter 12 may be fed by the medical professional through the inferior vena cava 40 of the liver 24 and into one of the upper hepatic veins 22 of the liver 24, for example, the right hepatic vein 22a, left hepatic vein 22b, or middle hepatic vein 22c. The catheter 12 may be further fed from the upper hepatic veins 22 into coextending lower blood vessels 42 branching from the upper hepatic veins 22 and which contact with the hepatic tissue 44. For example, a first catheter 12a may be fed into one of the upper hepatic veins 22 and terminate in a lower blood vessel 42a while a second catheter 12b is fed into the same upper hepatic vein 22 as the first catheter 12a but terminate in a lower blood vessel 42b sharing adjacent tissue with the lower blood vessel 42a. In this manner, the first catheter 12a and second catheter 12b are in relatively close proximity, about 5-30 mm, allowing an electric field 46 to be created between the first catheter 12a and the second catheter 12b as further discussed below.

Referring now to FIG. 3, each catheter 12 may have a construction facilitating dispersion of the viral vector 18 through the catheter 12 as well as electroporation of the hepatic cells 44 as described below.

The catheter 12 may include a thin, flexible tube having an outer wall 50 made from a medical grade material such as vinyl, rubber latex, and silicone. The outer wall 50 has sufficient flexibility to flex with flexure of the catheter 12 without holding a bent shape and without changing the stiffness of the outer wall 50. The outer wall 50 may have an outer diameter of 1.5-3 mm and an inner dimeter of 0.8-2.5 mm. The catheter 12 may be consistent with a 5 French gauge catheter, 6 French gauge catheter, 7 French gauge catheter, 8 French gauge catheter or 9 French gauge catheter.

The outer wall 50 may provide an inner lumen 52 allowing for the flow of fluids therethrough. For example, the internal lumen 52 may allow for the passage of the viral vectors 18 from the proximal port 30 extending outside the body to a terminal end 54 of the catheter 12 positioned within the lower blood vessel 42. The terminal end 54 may be a straight end terminating at a rounded enclosed tip or catheter cap. The terminal end 54 may also support a balloon 38 as further described below.

When installed within the lower blood vessel 42, a distal end 56 of the catheter 12 may provide an active section 60 delivering the viral vector 18 through the outer wall 50 and into the lower blood vessel 42 and further flanked by spaced apart balloons 38, as further discussed below. The outer wall 50 of the catheter 12 may include one or more exit ports 58 within the active section 60 of the catheter 12 allowing for the egress of viral vectors 18 injected into the catheter 12, flowing through the inner lumen 52, and flowing outward into the surrounding hepatic cells 44. The exit ports 58 may be approximately 0.1-0.4 mm in diameter or may be approximately ¼ to ½ of the inner diameter of the catheter 12. It is understood that any number of exit ports 58 may be included within the catheter outer wall 50 depending on the desired length of the active section 60, and in any configuration around a circumference of the outer wall 50.

The exit ports 58 may be linearly aligned along a longitudinal axis 62 of the catheter 12, or alternatively, the exit ports 58 may be staggered in varying positions around a circumference of the outer wall 50 along the longitudinal axis 62 of the catheter 12. The exit ports 58 may be substantially centered longitudinally within the active section 60. For example, a single exit port 58 may be centered within the active section 60 or more than one exit ports 58 may be spaced symmetrically about the center the active section 60 along substantially the entire length of the active section 60.

Alternatively, the outer wall 50 may be a porous material having minute openings allowing the viral vectors 18 to permeate the outer wall 50 of the tube and disseminate into the surrounding hepatic cells 44.

Generally, it is understood that the active section 60 allows for the egress of the viral vectors 18 from the inner lumen 52 into the hepatic tissue 44 surrounding the active section 60 of the catheter 12.

The dispersion of viral vectors 18 volumes may be contained by at least two balloons 38, and preferably a pair of balloons 38a, 38b, spaced apart and flanking the active section 60 of the catheter 12 delivering the viral vector 18. A distal balloon 38a may be positioned at or near the terminal end 54 of the catheter 12 and a proximal balloon 38b may be positioned upstream from the terminal end 54 on the proximal side of the active section 60.

The balloon 38 may be integrally molded with the catheter 12, for example, built within or as part of the outer wall 50 of the catheter 12, or may be bonded to the outer wall 50 of the catheter 12, for example, by a curable adhesive sealing an outer perimeter of the balloon 38 material to the outer wall 50 to create an airtight seal. The balloon 38 may be made of a material which resiliently deforms under radial pressure, for example, polyethylene (PE), nylon, polyamide, polyether block amides (PEBAX), polyethylene terephthalate (PET), silicone, POC, polypropylene, polyether block PBT and the like. The balloon 38 may include multiple layers and/or be coextruded and may also include additional fiber reinforcements.

The pair of balloons 38a, 38b may be inflated simultaneously by injecting gas or liquid such as air or saline into the balloon inflation port 34 at the proximal end 17 of the catheter 12 and through the balloon inflation tube 36 extending longitudinally with the catheter 12. The balloon inflation tube 36 may be integrated with the catheter 12, for example, molded within the walls of the catheter 12, bonded to the catheter 12, or separate from the catheter 12. It may be desired to include a separate balloon inflation tube 36 from the inner lumen 52 to independently control inflation or deflation of the balloons 38a, 38b while also using the inner lumen 52 as a fluid channel for the delivery of viral vectors 18. In this respect gas or liquid may flow through a balloon lumen that is separate from the inner lumen 52 of the catheter 12. Alternatively, the gas or liquid may flow through the same tube as the inner lumen 52 of the catheter 12.

The balloon 38 may be constructed as described above and as described in U.S. Pat. Nos. 8,603,064 and 7,060,051, both of which are hereby incorporated by reference.

The balloons 38a, 38b may secure the positioning of the catheter 12 within the lower blood vessel 42 by engaging the inner walls of the lower blood vessel 42 thus anchoring the catheter 12 to the lower blood vessel 42 when inflated, and then deflated for removal of the catheter 12 from the lower blood vessel 42 and from the body.

The balloons 38a, 38b also provide additional benefit by localizing the dispersion of the viral vectors 18 to a gene delivery area 64 substantially longitudinally bounded by the pair of inflated balloons 38a, 38b. In this respect, when viral vector 18 is injected into the inner lumen 52 of the catheter 12, the inflated balloons 38a, 38b prevent the viral vector 18 from flowing downstream or upstream through the lower blood vessel 42. Therefore, the viral vectors 18 are encouraged to be absorbed into the nearby surrounding hepatic tissue, or may flow into smaller lateral vessels and capillaries to then be absorbed into the nearby surrounding hepatic tissue, instead of returning up the vein toward the proximal port 30 or down the vein from the terminal end 54 of the catheter 12.

The inflated balloons 38a, 38b also block blood flow between the inflated balloons 38 during gene delivery.

Figure 4:
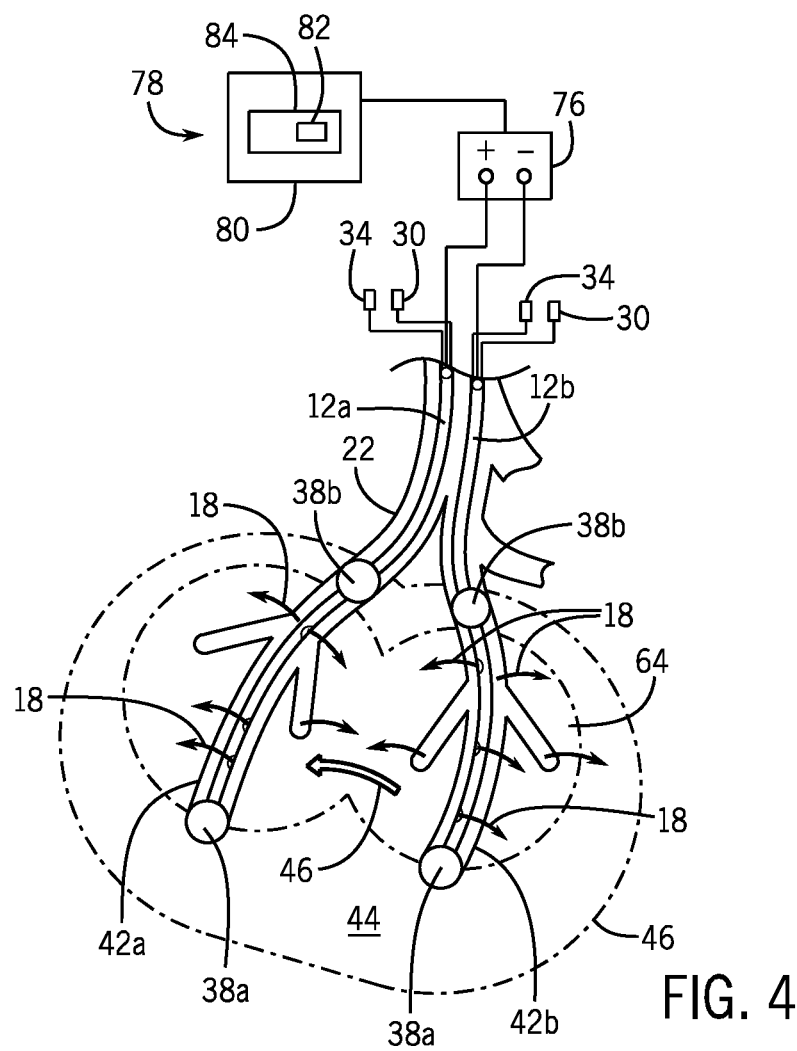
FIG. 4 is an enlarged view of FIG. 2 showing the pair of catheters inserted into the lower hepatic veins of the liver and providing dispersion of viral vectors from the catheters into a gene delivery area while an electric field is created around the catheters.

Referring to FIGS. 3 and 4, each catheter 12 may support an antenna providing an electrical conductor 70, extending coaxially within the internal lumen 52 along the longitudinal axis 62 of the catheter 12. The internal electrical conductor 70 may also be coaxially positioned within the internal lumen 52 so that it does not block or obscure any of the exit ports 58, for example, it may be substantially centered within the lumen 52. The outer dimension of the internal electrical conductor 70 is less than the inner diameter of the outer wall 50 of the catheter 12 to provide clearance around the internal electrical conductor 70 for viral vector 18 to fill in and flow though and out. The internal electrical conductor 70 may extend substantially an entire length of the catheter 12, however, terminating before reaching the terminal end 54 of the catheter 12, or before the distal balloon 38b. The internal electrical conductor 70 is configured to carry electrical charge and may be copper plated steel or stainless steel with or without an outer dielectric insulator permitting free passage of the electrical field but blocking electrical current flow and chemical reaction between the fluid and the material of the electrical conductor 70.

The internal electrical conductor 70 may be shielded above the active section 60, or above the proximal balloon 38a, by an insulator 72 layer, an outer conductor 73 layer, and an insulator shield or jacket 75. The outer conductor 73 layer may be connected to a ground potential while the internal electrical conductor 70 is connected to a power source. In this respect, the electric field is restricted to the dielectric and does not extend from the shielded section 74. For example, a shielded portion 74 may be a shielded cable, such as a coaxial cable, or a layered medical tubing with the internal electrical conductor 70 surrounded by a tubular insulating layer 72, for example, a solid plastic or a foam plastic such as solid polytetrafluoroethylene (PTFE) or solid polyethylene (PE) dielectric, and further surrounded by a tubular outer conductor 73, for example, a metal braided shield such as braided copper, aluminum or stainless steel wire, which may be plated or multi-layered, and may be further surrounded by an insulating shield or jacket 75, for example, a solid plastic such as polyvinyl chloride (PVC) which may be sealed around the outer conductor 73 to prevent reaction with fluids and the like.

The internal electrical conductor 70 may extend into the active section 60 with the insulator 72, outer conductor 73, and insulator jacket 75 removed. In this respect, the electric fields in the shielded portion 74 above the active section 60 are reduced and do not extend into the surrounding hepatic tissue 44 until reaching the active section 60 of the catheter 12. Alternatively, the internal electrical conductor 70 may remain insulated in the active section 60 with only the outer conductor 73 and insulator jacket 75 removed. In this respect, electrical current is blocked from flowing into the surrounding hepatic tissue 44 and the internal electrical conductor 70 is not exposed to chemical reaction with the hepatic tissue 44. It is understood that the shielded portion 74 may still have an outer dimension less than the inner diameter of the outer wall 50 of the catheter 12 to provide clearance therearound for flow of viral vector 18.

Figure 5:
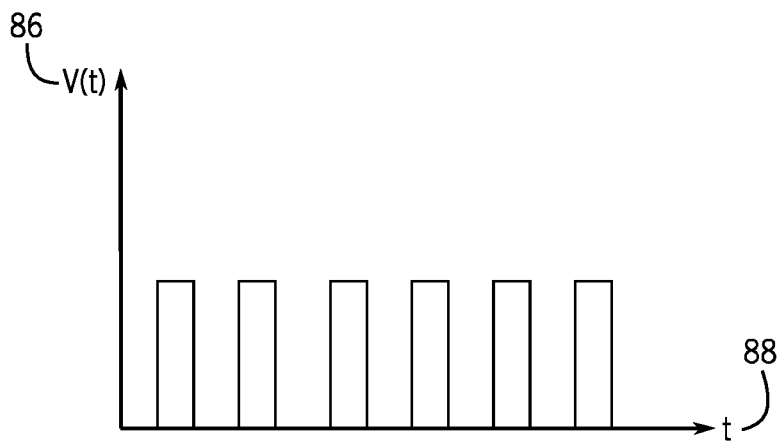
FIG. 5 is a chart showing a pattern of electrical field pulses delivered to the conductor electrodes of the pair of catheter.

Referring also to FIG. 5, the internal electrical conductors 70a, 70b of each catheter 12a, 12b may be used in conjunction with a pulse generator 76 providing a pulsed electrical charge to the internal electrical conductors 70a, 70b. For example, the pulse generator 76 may deliver a direct current (DC) in the form of a repeated pulse or burst of an appropriate current amplitude and duration to one of the internal electrical conductors 70a, 70b to create a voltage (i.e., potential difference) between the internal electrical conductors 70a, 70b. An electric pulse may be applied to one of the internal electrical conductors 70a, 70b receiving positive direct current while the other of the internal electrical conductors 70a, 70b acts as the return, negatively biased electrode. The shield or outer conductor 73 is grounded halfway between the two potential biases.

Pulse generators 76 suitable for in vivo electroporation as taught herein are sold by ECM under the trade name "830 square wave electroporation system". Other pulse generators 76 are also commercially available and may be used with the present invention.

As illustrated in FIG. 5, the electric pulses may be repeated square pulses created by the pulse generator 76. It is understood that the electric pulses may take other shapes such as spikes or round waves. An electronic control circuit 78 may communicate with the pulse generator 76 to receive a preset voltage output and pulse length from the medical professional. The electronic control circuit 78 may hold, for example, a microprocessor 80 for executing a program 82 held in a stored memory 84.

The microprocessor 80 may also receive input data from the medical professional such as a distance between internal electrical conductors 70a, 70b, or a cross-sectional area between internal electrical conductors 70a, 70b, and execute the program 82 held in the stored memory 84 to output a voltage output 86 and pulse duration 88 to be used for effective pulse delivery, for example, using a lookup table.

It is understood that internal electrical conductors 70a, 70b may be angled with respect to each other and may not be perfectly parallel along the active section 60. In this manner, the medical professional may take the largest distance or area therebetween or take an average distance or area therebetween in determining the distance between internal electrical conductors 70a, 70b and an effective pulse delivery.

The voltage output 86 may be selected so that the electric field 46 created between the internal electrical conductors 70a, 70b achieves or exceeds an efficacious electric field strength. For example, if the electric field 46 is too high, this can result in cell death through irreversible electroporation. Alternatively, if the electric field strength is too low, the transmembrane potential required to permeabilize the cell membrane (typically 0.7 V) cannot be reached.

The pulse duration 88 may also be selected so that the electric field 46 created between the internal electrical conductors 70a, 70b achieves or exceeds an efficacious electric field 46 strength. For example, if the pulse length is too short, (microseconds), the membrane capacitance may not charge up high enough to reach the required transmembrane potential. An efficacious electric field 46 strength may be coextensive with the gene delivery area 64.

It has found that for gene delivery (compared to drug delivery), a combination of low electric field strength and long pulse length has been effective. For example, electric field intensities between 100-200 V/cm and pulse durations of 38-100 msec; and electric field intensities between 200-275 V/cm and pulse duration of about 50 msec have been found to be effective. Other parameters, which determine the efficacy of the delivery of viral vectors 18 into hepatic cells 44 are field strength, pulse length, shape of the pulse and number of pulses.

The parameters of the electroporation described above may be as further described in Methods in Molecular Medicine, Vol. 37: Electrically Mediated Delivery of Molecules to Cells, Edited by: M. J. Jaroszeski, R. Heeller, and R. Gilbert, Humana Press, Inc., Totowa, NJ, and hereby incorporated by reference.

Figure 6:
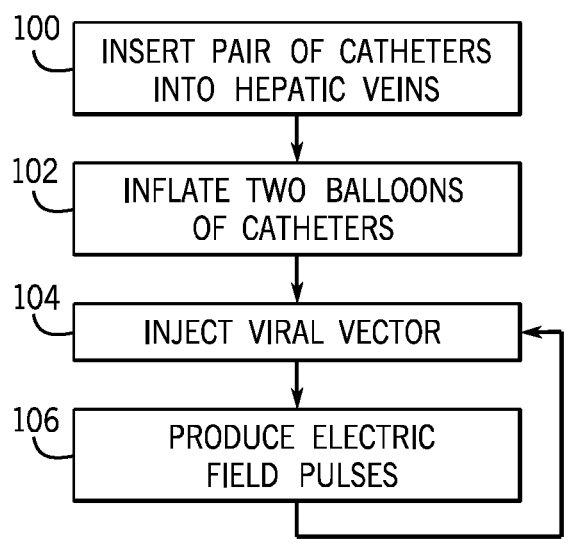
FIG. 6 is a flow chart showing the method steps of gene therapy according to the present invention.

Referring now to FIG. 6, as noted above, the present invention uses a pair of catheters 12a, 12b to provide more efficient gene delivery eliminating the need for large vector doses or a highly invasive procedure. Such a procedure can use a pair of minimally invasive vascular catheters 12a, 12b catheterizing lower blood vessels 42a, 42b of the liver 24 to perform direct gene delivery into the target liver with greater efficacy. To further enhance the efficiency of gene delivery for a large tissue area, the catheters 12a, 12b simultaneously electroporate the hepatic cells 44 between adjacent electrodes to open temporary pores in the cell membrane allowing the vector 18 to readily enter the cells.

As indicated by process block 100, a first catheter 12a may be inserted through a venous access site 20, for example, the jugular vein 20b, through a small incision at the neck of the human patient 14. The medical professional may use a guidewire and/or real-time visual imaging such as ultrasound or x-ray (fluoroscopy) to assist with the catheterization of the hepatic vein 22. A second catheter 12b may be similarly inserted through the venous access site 20 to catheterize the hepatic vein 22.

As indicated by process block 102, once the catheters 12a, 12b are properly positioned within adjacent, coextending lower blood vessels 42a, 42b of the liver 24, the respective balloons 38a, 38b may be inflated by injecting gas or fluid such as air or saline through the balloon inflation port 34 and through the inflation tube 36 in order to secure the catheters 12a, 12b in position, prevent further blood flow between the balloons 38a, 38b, and to isolate the gene delivery area 64. The balloons 38a, 38b of each catheter 12a, 12b may inflate simultaneously and to a similar extent such that the inflated balloons 38a, 38b of each respective catheter 12a, 12b are a similar size. In this respect the balloons 38a, 38b of the catheter 12a may be a different size from the balloons 38a, 38b of the catheter 12b to accommodate for different inner diameter sizes of the blood vessels 42a, 42b.

Optionally, saline may be injected into the proximal ports 30 of the catheters 12a, 12b to wash the inner lumen 52 and gene delivery area 64 from obstructive blood and tissues.

Then, as indicated by process block 104, the viral vector 18 may be injected into the proximal ports 30 of the catheters 12a, 12b in order to fill the inner lumen 52 of the catheters 12a, 12b with the viral vector 18 and to disseminate the vector 18 through the exit ports 56 of the outer wall 50 of the catheters 12a, 12b, and further through the vascular walls of the lower blood vessels 42a, 42b, and into the gene delivery area 64 surrounding the catheters 12a, 12b. It is understood that the gene delivery area 64 may comprise of regions emanating from and surrounding the active section 60 of each catheter 12a, 12b.

As indicated by process block 106, the medical professional may consider the location and distance between the catheters 12a, 12b using visual imaging such as ultrasound or x-ray to determine a desired voltage output 86 and pulse duration 88 to be outputted by the pulse generator 76. The medical professional may program the pulse generator 76 to elicit a direct current in short pulses, for example, square waves as illustrated in FIG. 5, to the internal electrical conductors 70 of the catheters 12a, 12b to therefore create an electric field 46 surrounding the catheters 12a, 12b. It is understood that the electric field 46 may comprise of a region surrounding the catheters 12a, 12b and extending across the catheters 12a, 12b, the tissue area coextensive or greater than the gene delivery area 64.

The electroporation of the gene delivery area 64 provided by the electric field 46 allows for the hepatic cells 44 in the gene delivery area 64 to be more susceptible to viral intake. In this respect, the catheters 12 allow for simultaneous or nearly simultaneous delivery of genes to cells with electroporation of the cells extending between the pair of catheters 12. It is contemplated that the drug delivery described above may be performed once or may be conducted as repeated treatments as necessary.

It is understood that the gene therapy delivery system 10 may be performed on any mammal and of any size, for example, both small and large mammals.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can

What we claim is:

1. A gene delivery system for delivering viral vectors containing genetic material into cells of a patient, comprising:
    a first electrode insertable into a first blood vessel of the patient;
    a second electrode insertable into a second blood vessel of the patient; and
    an electric pulse generator configured to deliver at least one electric pulse to at least one of the first and second electrodes to apply a voltage between the first and second electrodes and create an electric field across the first and second electrodes and on cells surrounding the electrodes to increase the transduction rate of viral vectors into the cells of the patient;
    wherein each of the first and second electrodes comprises a coaxial conductor having an inner coaxial conductive element and an outer coaxial conductive element, and
    wherein the outer coaxial conductive element is absent from the coaxial conductor at a distal portion of the coaxial conductor to allow transmission of an electric field for electroporation.

2. The system of claim 1 further comprising
    a first catheter comprising a distal end defining a delivery portion and at least one passageway through a lumen of the catheter for the delivery of at least one viral vector wherein the first electrode extends along the first catheter; and
    a second catheter comprising a distal end defining a delivery portion and at least one passageway through a lumen of the catheter for the delivery of at least one viral vector wherein the second electrode extends along the second catheter.

3. The system of claim 1 wherein the at least one electrical pulse is configured to produce an electric field strength between the first and second electrode and a pulse duration that increases the delivery of viral vectors into cells surrounding the electrodes according to a processor executing a program held in stored memory.

4. The system of claim 3 wherein the at least one electrical pulse is configured to produce an electric field strength between the first and second electrode that is 100-200 V/cm.

5. The system of claim 4 wherein the at least one electrical pulse has a pulse duration of 38-100 msec.

6. The system of claim 3 wherein the at least one electrical pulse is configured to produce an electric field strength between the first and second electrode that is 200-275 V/cm.

7. The system of claim 6 wherein the at least one electrical pulse has a pulse duration of about 50 msec.

8. The system of claim 3 wherein the shape of the electric pulse and number of pulses of the electrical charge are configured to produce an electric field increasing the delivery of viral vectors into the cells surrounding the first and second electrodes according to a processor executing a program held in stored memory.

9. The system of claim 1 wherein the at least one viral vector contains foreign, functional genes.

10. A method for delivering one or more viral vectors containing genetic material into cells of a patient, comprising:
    inserting a first electrode into a first blood vessel of the patient, the first electrode comprising a first coaxial conductor having an inner coaxial conductive element and an outer coaxial conductive element, the outer coaxial conductive element being absent from the first coaxial conductor at a distal portion of the first coaxial conductor to allow transmission of an electric field for electroporation;
    inserting a second electrode into a second blood vessel of the patient the second electrode comprising a second coaxial conductor having an inner coaxial conductive element and an outer coaxial conductive element, the outer coaxial conductive element being absent from the second coaxial conductor at a distal portion of the second coaxial conductor to allow transmission of the electric field;
    injecting the at least one viral vector into the patient; and
    delivering at least one electrical pulse to at least one of the first and second electrodes configured to apply a voltage between electrodes and create the electric field across the first and second electrodes and on cells surrounding the electrodes to increase the transduction rate of viral vectors into the cells surrounding the electrodes of the patient.

11. The method of claim 10 further comprising
    providing a first catheter comprising a distal end to define a delivery portion, at least one passageway through a lumen of the catheter for the delivery of the at least one viral vector through the delivery portion, and a proximal end having a therapeutic injection port;
    inserting the first catheter into the first blood vessel of the patient;
    providing a second catheter comprising a distal end to define a delivery portion, at least one passageway through a lumen of the catheter for the delivery of at least one viral vector through the delivery portion, and a proximal end having a therapeutic injection port; and
    inserting the second catheter into the second blood vessel of the patient.

12. The method of claim 10 wherein the at least one electrical pulse is configured to produce an electric field strength between the first and second electrode and a pulse duration that increases the delivery of viral vectors into the cells surrounding the first and second electrodes according to a processor executing a program held in stored memory.

13. The method of claim 12 wherein the at least one electric pulse is configured to produce an electric field strength between the first and second electrode that is 100-200 V/cm.

14. The method of claim 13 wherein the at least one electrical pulse has a pulse duration of 38-100 msec.

15. The method of claim 12 wherein the at least one electric pulse is configured to produce an electric field strength between the first and second electrode that is 200-275 V/cm.

16. The system of claim 15 wherein the at least one electrical pulse has a pulse duration of about 50 msec.

17. The method of claim 10 wherein the at least one viral vector delivers foreign, functional genes into the cells of the patient.

18. The method of claim 10 wherein the first and second electrodes are inserted into first and second blood vessels located within a vascularized organ, tissue, or tumor.

19. The method of claim 18 wherein the first and second electrodes are inserted into first and second blood vessels located in a liver of the patient.

* * * * *